US011576950B2

(12) United States Patent
Cox et al.

(10) Patent No.: US 11,576,950 B2
(45) Date of Patent: Feb. 14, 2023

(54) METHODS OF USING AND COMPOSITIONS CONTAINING DULAGLUTIDE

(71) Applicant: Eli Lilly and Company, Indianapolis, IN (US)

(72) Inventors: David Andrew Cox, Batesville, IN (US); Zvonko Milicevic, Vienna (AT); Lai San Tham, La Crystal (SG); David Bradley Woodward, Fishers, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 16/763,269

(22) PCT Filed: Nov. 13, 2018

(86) PCT No.: PCT/US2018/060716
§ 371 (c)(1),
(2) Date: May 12, 2020

(87) PCT Pub. No.: WO2019/103875
PCT Pub. Date: May 31, 2019

(65) Prior Publication Data
US 2020/0330558 A1    Oct. 22, 2020

Related U.S. Application Data

(60) Provisional application No. 62/589,244, filed on Nov. 21, 2017.

(51) Int. Cl.
*A61K 38/00* (2006.01)
*A61K 38/26* (2006.01)
*A61P 3/10* (2006.01)

(52) U.S. Cl.
CPC ........... *A61K 38/26* (2013.01); *A61P 3/10* (2018.01)

(58) Field of Classification Search
CPC ........ A61K 38/26; A61K 47/12; A61K 47/26; A61K 9/08; A61P 3/10
See application file for complete search history.

(56) References Cited

U.S. PATENT DOCUMENTS

| | | | |
|---|---|---|---|
| 2004/0053370 A1 | 3/2004 | Glaesner et al. | |
| 2007/0036806 A1 | 2/2007 | Glaesner et al. | |
| 2009/0232807 A1 | 9/2009 | Glaesner et al. | |
| 2010/0196405 A1 | 8/2010 | Glaesner et al. | |
| 2020/0171129 A1 | 6/2020 | Botros | |

FOREIGN PATENT DOCUMENTS

| | | | | |
|---|---|---|---|---|
| WO | 2009009562 A2 | 1/2009 | | |
| WO | WO-2009009562 A2 * | 1/2009 | ............ | A61K 47/18 |
| WO | 2016168388 A2 | 10/2016 | | |

OTHER PUBLICATIONS

Smith et al. Dulaglutide (Trulicity): The Third Once-Weekly GLP-1 Agonist. P T. Jun. 2016; 41(6): 357-360 (Year: 2016).*
A Study of LY2189265 Compared to Sitagliptin in Participants With Type 2 Diabetes Mellitus on Metformin. Clinical trials.gov (Year: 2015).*
A Study of LY2189265 Compared to Sitagliptin in Participants With Type 2 Diabetes Mellitus on Metformin. Results (Year: 2015).*
Zhang et al. Efficacy and safety of dulaglutide in patients with type 2 diabetes: a meta-analysis and systematic review. Scientific report Jan. 2016. (Year: 2016).*
Barrington 2009. Safety, Tolerability, Pharmacokinetics, and Insulinotropic Activity of Single Subcutaneous Doses of LY2189265, a Long-Acting Glucagon-Like Peptide 1 (GLP-1) Analog in Healthy Subjects (Year: 2009).*
Reaney, M., et al, Treatment satisfaction in people with type 2 diabetes mellitus treated with once-weekly dulaglutide: data from the AWARD-1 and AWARD-3 clinical trials, *Diabetes, Obesity and Metabolism*, 2015;17(9), 896-903.
Singh S, et al, Glucagon-like peptide-1 receptor agonists compared with basal insulins for the treatment of type 2 diabetes mellitus: a systematic review and meta-analysis, *Diabetes, Obesity and Metabolism*, 2016.
Skrivanek Z., et al, Application of adaptive design methodology in development of a long-acting glucagon-like peptide-1 analog (dulaglutide): statistical design and simulations, *Journal of Diabetes Science and Tech*, 2012;vol. 6, Issue 6.
Skrivanek Z., et al, Dose-finding results in an adaptive trial of dulaglutide combined with metformin in type 2 diabetes (AWARD-5); *American Diabetes Association 73rd Meeting*, Jun. 2013.
Skrivanek Z., et at, Dose-finding results in an adaptive, seamless, randomized trial of once-weekly dulaglutide combined with metformin in type 2 diabetes patients (AWARD-5), *Diabetes, Obesity and Metabolism*., 2014;16(8):748-756.
Spencer K., et al, Operational challenges and solutions with implementation of an adaptive seamless phase 2/3 study, *Journal of Diab Science and Tech*, 2012; vol. 6, Issue 6.
Terauchi, Y., et al, Monotherapy with the once weekly GLP-1 receptor agonist dulaglutide for 12 weeks in Japanese patients with type 2 diabetes: dose-dependent effects on glycaemic control in a randomised, double-blind, placebo-controlled study, *Endocrine journal*, 2014;EJ14-0147.
Trulicity [Prescribing Information]. Indianapolis, IN: Eli Lilly and Company, 2017. Available at: http://pl.lilly.com/us/trulicity-uspl.pdf. Accessed Oct. 18, 2017.
Trulicity [summary of product characteristics (SmPC)]. Houten, The Netherlands; 2017. Available at http://www.ema.europe.ou.docs/en_GB/document/library/EPAR_Product_information/human/002825/WC500179470.pdf.
Tuttle, K. R., et al, Effects of once-weekly dulaglutide on kidney function in patients with type 2 diabetes in phase II and III clinical trials, *Diabetes, Obesity and Metabolism*, 2017, 19(3), 436-441.
Umpierrez, G., et al, The effects of LY2189265, a long-acting glucagon-like peptide-1 analogue, in a randomized, placebo-controlled, double-blind study of overweight/obese patients with type 2 diabetes: the EGO study, *Diabetes, Obesity and Metabolism*, 2011;13(5), 418-425.

(Continued)

*Primary Examiner* — Aradhana Sasan
*Assistant Examiner* — Mercy H Sabila
(74) *Attorney, Agent, or Firm* — Matthew T. Lord

(57) ABSTRACT

The present invention relates to methods of using new doses of dulaglutide and compositions containing such higher doses of dulaglutide.

3 Claims, No Drawings
Specification includes a Sequence Listing.

(56) References Cited

OTHER PUBLICATIONS

Umpierrez G., et al, Efficacy and safety of dulaglutide monotherapy versus metformin in type 2 diabetes in a randomized controlled trial (AWARD-3), *Diabetes Care*, 2014;37(8):2168-2176.
Umpierrez G., et al, Relationship between weight change and glycaemic control in patients with type 2 diabetes receiving once-weekiy dulaglutide treatment, *Diabetes, Obesity and Metabolism*, 2016;18(6), 615-622.
Usborne, A., et al, An investigative study of pancreatic exocrine biomarkers, histology, and histomorphometry in male Zucker diabetic fatty (ZDF) rats given dulaglutide by subcutaneous injection twice weekly for 13 weeks, *Toxicologic pathology*, 2015;43(8), 1093-1102.
Vahle, J. L., et al, Effects of the GLP-1 receptor agonist dulaglutide on the structure of the exocrine pancreas ofcynomolgus monkeys, *Toxicologic pathology*, 2015;43(7), 1004-1014.
Vahle, J. L., et al, Effects of dulaglutide on thyroid C cells and serum calcitonin in male monkeys, *Endocrinology*, 2015;156(7), 2409-2416.
Weinstock R.S., et al, Safety and efficacy of once-weekiy dulaglutide versus sitagliptin after 2 years in metformin-treated patients with type 2 diabetes (AWARD-5): a randomized, phase III study, *Diabetes, Obesity and Metabolism*. 2015;17(9): 849-858.
Wysham C. et al, Efficacy and safety of dulaglutide added onto pioglitazone and metformin versus exenatide in type 2 diabetes in a randomized controlled trial (AWARD-1), *Diabetes Care*, 2014;37(8):2159-2167.
Wysham, C., et al, Baseline factors associated with glycaemic response to treatment with once-weekly dulaglutide in patients with type 2 diabetes, *Diabetes, Obesity and Metabolism*, 2016;18(11), 1138-1142.
Yu, M., et al, Patient-reported outcomes in patients with type 2 diabetes treated with dulaglutide added to titrated insulin glargine (AWARD-9), *Clinical Therapeutics*, 2017;39(11), 2284-2295.
Alatorre, C., et al, Treatment patterns in patients with type 2 diabetes mellitus treated with glucagon-like peptide-1 receptor agonists: Higher adherence and persistence with dulaglutide compared with once-weekly exenatide and liraglutide, *Diabetes, Obesity and Metabolism*, 2017;19(7), 953-961.
Anderson J, et al, Dulaglutide in the treatment of adult type 2 diabetes: a perspective for primary care providers, Postgraduate Medicine, Dulaglutide in the treatment of adult type 2 diabetes: a perspective for primary care providers, Postgraduate Medicine, 2016;128:8, 810-821, DOI: 10.1080/00325481.2016.1218260, https://doi.org/10.1080/00325481.2016.1218260.
Barrington P., et all, A 5-week study of the pharmacokinetics and pharmacodynamics of LY2189265, a novel, long acting glucagon-like peptide-1 analogue, in patients with type 2 diabetes, *Diabetes, Obesity and Metabolism*. 2011;13(5):426-433.
Barrington P., et al, LY2189265, a long-acting glucagon-like peptide-1 analogue, showed a dose-dependent effect on insulin secretion in healthy subjects. *Diabetes, Obesity and Metabolism*. 2011;13(5):434-438.
Bibeau, W. S., et al, Impact of out-of-pocket pharmacy costs on branded medication adherence among patients with type 2 diabetes. *Journal of managed care & specialty pharmacy*, 2016;22(11), 1338-1347.
Blonde L., et al, Once-weekly dulaglutide versus bedtime insulin glargine, both in combination with prandial insulin lispro, in patients with type 2 diabetes (AWARD-4): a randomised, open-label, phase 3, noninferiority study, *Lancet*. 2015;385(9982):2057-2066.
Boustani, M. A., et al, Similar efficacy and safety of once-weekly dulaglutide in patients with type 2 diabetes aged≥ 65 and< 65 years. *Diabetes, Obesity and Metabolism*, 2016;18(8), 820-828.
Boye, K. S., et al, Associations between adherence and outcomes among older, type 2 diabetes patients: evidence from a Medicare Supplemental database. *Patient preference and adherence*, 2016;10, 1573.

Byrd R. A., et al, Chronic toxicity and carcinogenicity studies of the long-acting GLP-1 receptor agonist dulaglutide in rodents, *Endocrinology*, 2015;156(7), 2417-2428.
Chien, J. et, al, LY2189265, a long-acting glucagon-like peptide 1 (GLP-1) analog, does not affect gastric emptying of acetaminophen after multiple dosing in healthy subjects, *Diabetes*, Jun. 2010; vol. 59, pp. A164-A164, Amer Diabetes Assoc.
Casagrande S., et al, The prevalence of meeting A1C, blood pressure, and LDL goals among people with diabetes, 1988-2010, *Diabetes Care*, 2013;36(8):2271-2279.
Davidson, J. A., et al, Efficacy and safety of dulaglutide in Hispanic/Latino patients with type 2 diabetes in the Award clinical program, *Endocrine Practice*, 2016;22(12), 1406-1414.
De La Peña, A., et al, Once-weekly dulaglutide 1.5 mg restores insulin secretion in response to intravenous glucose infusion, *Diabetes, Obesity and Metabolism*, 2016;19(4), 517-523.
De La Peña, A., et al, No dose adjustment is recommended for digoxin, warfarin, atorvastatin or a combination oral contraceptive when coadministered with dulaglutide, *Clinical Pharmacokinetics*, 2017;56(11), 1415-1427.
Dilla, T., et al, The cost-effectiveness of dulaglutide versus liraglutide for the treatment of type 2 diabetes mellitus in Spain in patients with BMI≥ 30 kg/m2, *Journal of Medical Economics*, 2016;20(5), 443-452.
Divino, V., et al, GLP-1 RA treatment patterns among type 2 diabetes patients in five European countries, *Diabetes Therapy*, 2017;8(1), 115-128.
Dungan K.M., et al, Once-weekly dulaglutide versus once-daily liraglutide in metformin-treated patients with type 2 diabetes (AWARD-6): a randomised, open-label, phase 3, non-inferiority trial, *Lancet*, 2014;384(9951), 1349-1357.
Dungan K., et al, Achieving the composite endpoint of glycated haemoglobin> 7.0%, no weight gain and no hypoglycaemia in the once-weekly dulaglutide AWARD programme, *Diabetes, Obesity and Metabolism*, Jan. 2016;18(1), 49-55.
Dungan, K.M., et al, A 24-week study to evaluate the efficacy and safety of once-weekly dulaglutide added on to glimepiride in type 2 diabetes (AWARD-8). *Diabetes, Obesity and Metabolism*, May 2016;18(5), 475-482.
Edwards K.L. and Minze, M.G., Dulaglutide: an evidence-based review of its potential in the treatment of type 2 diabetes, *Core evidence*, 2015;10, 11.
Fahrbach J.L., et al, Network meta-analysis accurately predicted the outcome of a subsequent randomised trial comparing once weekly dulaglutide 1.5 mg and once daily liraglutide 1.8 mg, *International Journal of Clinical Practice*, 2016;70(3), 218-221.
Ferdinand, K. C., et al, Effects of the once-weekly glucagon-like peptide-1 receptor agonist dulaglutide on ambulatory blood pressure and heart rate in patients with type 2 diabetes mellitus, *Hypertension*, 2014;64(4), 731-737.
Ferdinand K.C., et al, Cardiovascular safety for once-weekly dulaglutide in type 2 diabetes: a pre-specified meta-analysis of prospectively adjudicated cardiovascular events, *Cardiovasc Diabetol*, 2016;15:38.
Frias, J.P., et al, Efficacy and Safety of an Expanded Dulaglutide Dose Range: A Phase 2, Placebo-Controlled Trial in patients with type 2 diabetes using Metformin, *Diabetes, Obesity and Metabolism.*, 2019;21:2048-2057.
Gallwitz, B., et al, Effect of once-weekly dulaglutide on glycated haemoglobin (HbA1c) and fasting blood glucose in patient subpopulations by gender, duration of diabetes, and baseline HbA1c, *Diabetes, Obesity and Metabolism.*, 2018;20, 409-418.
Geiger M.J., et al, An adaptive, dose-finding, seamless phase 2/3 study of a long-acting glucagon-like peptide-1 analog (dulaglutide): trial design and baseline characteristics, Journal of Diabetes Science and Technology, 2012;vol. 6,Issue 6.
Geiser, J. S., et al, Clinical pharmacokinetics of dulaglutide in patients with type 2 diabetes: analyses of data from clinical trials, *Clinical pharmacokinetics*, 2016,55(5), 625-634.
Gelhorn, H. L., et al, Evaluating preferences for profiles of GLP-1 receptor agonists among injection-naive type 2 diabetes patients in the UK, *Patient preference and adherence*, 2015;9, 1611.

(56) References Cited

OTHER PUBLICATIONS

Gelhorn, H. L., et al, Evaluating preferences for profiles of glucagon-like peptide-1 receptor agonists among injection-naive type 2 diabetes patients in Japan, *Patient preference and adherence*, 2016;10, 1337.

Gerstein H.C., et al, on behalf of REWIND Trial Investigators, Design and baseline characteristics of participants in the Researching cardiovascular Events with a Weekly INcretin in Diabetes (REWIND) trial on the cardiovascular effects of dulaglutide, *Diabetes, Obesity and Metabolism*. 2017;doi: 10.1111/dom.13028.

Giorgino F., et al, Efficacy and safety of once weekly dulaglutide versus insulin glargine in patients with type 2 diabetes on metformin and glimepiride (AWARD-2), *Diabetes Care*, 2015;38(12):2241-2249.

Glaesner W., et al., Engineering and characterization of the long-acting glucagon-like peptide-1 analogue LY2189265, an Fc fusion protein, *Diabetes Metab Res Rev.*, 2010;26(4):287-296.

Grunberger, G., et al, Monotherapy with the once-weekly GLP-1 analogue dulaglutide for 12 weeks in patients with type 2 diabetes: dose-dependent effects on glycaemic control in a randomized, double-blind, placebo-controlled study, *Diabetic Medicine*, 2012;29(10), 1260-1267.

Grunberger G., et al, Early fasting glucose measurements can predict later glycaemic response to once weekly dulaglutide, *Diabetic Medicine*, 2015;33(3), 391-394.

Heathman M., et al, The application of drug-disease and clinical utility models in the design of an adaptive seamless phase 2/3 study:Pli-87. *Clinical Pharmacology & Therapeutics*, 93, 2013.

Jendle J, et al, Insulin and GLP-1 analog combinations in type 2 diabetes mellitus: a critical review, Expert Opin Investig Drugs, 2012; Oct;21(10):1463-74. doi: 10.1517/13543784.2012.707190. Epub Jul. 16, 2012. PMID: 22799463.

Jendle J., et al, Efficacy and safety of dulaglutide in the treatment of type 2 diabetes: a comprehensive review of the dulaglutide clinical data focusing on the AWARD phase 3 clinical trial program, *Diabetes Metab Res Rev.* May 2016;32(8):776-790.

Jendle J., et al, Continuous glucose monitoring in patients with type 2 diabetes treated with glucagon-like peptide-1 receptor agonist dulaglutide in combination with prandial insulin lispro: an AWARD-4 substudy, *Diabetes, Obesity and Metabolism*, Jun. 2016;18(10), 999-1005.

Kuritzky L, et al, Safety and Efficacy of Dulaglutide, a once weekly GLP-1 receptor agonist, for the management of type 2 Diabetes, Postgraduate Medicine, 2014;126:6, 60-71, DOI: 10.3810/pgm.2014.10.2821, To link to this article: https://doi.org/10.3810/pgm.2014.10.2821.

Loghin, C., et al, LY2189265, a long-acting GLP-1 analog, does not prolong QTc interval in healthy subjects at supratherapeutic doses, *Diabetes* (vol. 60, pp. A299-A299), Jul. 2011.

Lorenz M., et al, Differential effects of glucagon-like peptide-1 receptor agonists on heart rate, *Cardiovasc Diabetol*, 2017;16(1):6.

Mari A., et al, Differential effects of once-weekly glucagon-like peptide-1 receptor agonist dulaglutide and metformin on pancreatic β-cell and insulin sensitivity during a standardized test meal in patients with type 2 diabetes, *Diabetes, Obesity and Metabolism.*, 2016;18(8):834-839.

Matfin, G., et al, Safe and effective use of the once weekly dulaglutide single-dose pen in injection-naïve patients with type 2 diabetes, *Journal of Diabetes Science and Technology*, 2015;9(5), 1071-1079.

Matza, L. S., et al, Physician perceptions of GLP-1 receptor agonists in the UK, *Current Medical Research and Opinion*, 2016;32(5), 857-864.

Milicevic Z., et al, Low incidence of anti-drug antibodies in patients with type 2 diabetes treated with once-weekly glucagon-like peptide-1 receptor agonist dulaglutide, *Diabetes, Obesity and Metabolism*, 2016;18(5), 533-536.

Nauck M., et al, Efficacy and safety of dulaglutide versus sitagliptin after 52 weeks in type 2 diabetes in a randomized controlled trial (AWARD-5), *Diabetes Care*, 2014;37(8):2149-2158.

Nauck M., et al, Assessment of pancreas safety in the development program of once-weekly GLP-1 receptor agonist dulaglutide, *Diabetes Care*, 2017;40(5):647-654.

Noriega J, et al, The Impact Of LY2189265 (Glp-1 Analog) On Glycemic Control In Hispanic And Non-Hispanic Caucasians With Uncontrolled Type 2 Diabetes: An Ego Study Analysis, *Journal Of Investigative Medicine*, Apr. 2010;vol. 58, No. 4, pp. 644-644.

Pechtner V., et al, A new approach to drug therapy: Fc-fusion technology, *Prim Health Care*, 2017;7(1).

Pozzilli P., et al, Placebo-controlled, randomized trial of the addition of once-weekly glucagon-iike peptide-1 receptor agonist dulaglutide to titrated daily insulin glargine in patients with type 2 diabetes (AWARD-9), *Diabetes, Obesity and Metabolism*, 2017;19(7), 1024-1031.

Dulaglutide—Trulicity prescription label. Highlights of prescribing information. Sep. 2020.

Supplementary Material to Frias, J. P., et al., Efficacy and safety of dulaglutide 3.0 mg and 4.5 mg versus dulaglutide 1.5 mg in metformin-treated patients with type 2 diabetes in a randomized controlled trial (AWARD-11). *Diabetes Care*, 44(3), 765-773 (2021)., available at https://doi.org/10.2337/llgshare_13315403.

\* cited by examiner

METHODS OF USING AND COMPOSITIONS CONTAINING DULAGLUTIDE

The present invention relates to the field of medicine. More particularly, the present invention relates to methods of using new doses of dulaglutide and compositions containing such higher doses of dulaglutide.

Dulaglutide, the active ingredient in Trulicity®, is a glucagon-like peptide-1 (GLP-1) receptor agonist (GLP-1 RA) that is approved for use as an adjunct to diet and exercise to improve glycemic control in patients with Type 2 diabetes (T2D). Two once weekly dulaglutide doses, 0.75 mg and 1.5 mg, were studied in the Phase 3 development program and received regulatory approval in the United States (US), European Union and other jurisdictions in 2014. Since their approval in 2014, these two doses of dulaglutide have been used to treat many patients with T2D, resulting in significant reductions in HbA1c with low risk of hypoglycemia, and reductions in body weight.

While therapy with currently approved doses of dulaglutide enabled the majority of patients included in the Phase 3 program to attain their glycemic targets (with or without use of other concomitant medications for T2D), significant numbers of patients receiving approved therapies today, including dulaglutide, are not reaching glycemic control goals (see, e.g., Stark Casagrande et al. The prevalence of meeting A1c, blood pressure, and LDL goals among people with diabetes, 1988-2010. *Diabetes Care.* 2013; 36(8):2271-2279). Therefore, there remains an important medical need to provide enhanced efficacy of pharmaceutical agents while also preserving an overall acceptable benefit/risk profile.

The doses, methods and compositions of the present invention seek to meet that need. The benefits of the present invention include providing additional glycemic control, as evidenced for example by further reductions in HbA1c, and/or weight loss as compared to the currently approved doses of dulaglutide. Moreover, the present invention provides such benefits while maintaining an acceptable profile of safety risks and adverse events.

Accordingly, the present invention provides a method of improving glycemic control in a subject having type 2 diabetes (T2D) and in need of additional glycemic control, comprising:
  a) identifying a subject having T2D and in need of further glycemic control
  b) administering to said subject a first dose of dulaglutide once weekly for a minimum of four weeks; and
  c) increasing the dose to a second dose,
wherein the first dose is selected from the group consisting of 1.5 and 3.0 mg once weekly, and the second dose is selected from the group consisting of 3.0 and 4.5 mg once weekly.

In another aspect, the present invention provides a method of improving glycemic control in a subject having type 2 diabetes (T2D) and in need of further glycemic control, comprising:
  a) identifying a subject having T2D and in need of further glycemic control;
  b) administering to said subject 0.75 mg of dulaglutide once weekly for a minimum of four weeks;
  c) administering to said subject 1.5 mg of dulaglutide once weekly for a minimum of four weeks; and
  d) administering to said subject 3.0 mg once weekly.

In certain embodiments the method further comprising increasing the 3.0 mg dose to a 4.5 mg once weekly after the subject has been treated with the 3.0 mg dose for a minimum of four weeks.

In another aspect, the present invention provides a method of improving glycemic control in a subject having type 2 diabetes (T2D) and being treated with a 1.5 mg dose of dulaglutide once weekly but in need of further glycemic control, comprising: increasing the dose of dulaglutide being administered to 3.0 mg once weekly.

In another aspect, the present invention provides a method of improving glycemic control in a subject having type 2 diabetes (T2D) and being treated with a 3.0 mg dose of dulaglutide once weekly but in need of further glycemic control, comprising: increasing the dose of dulaglutide being administered to 4.5 mg once weekly.

In another aspect, the present invention provides an improved method for administering dulaglutide to a subject having T2D and in need of further glycemic control, wherein the improvement comprises administering 1.5 mg of dulaglutide once weekly for a minimum of four weeks, and then increasing the dose to 3.0 mg once weekly.

In another aspect, the present invention provides an improved method for administering dulaglutide to a subject having T2D and in need of further glycemic control, wherein the improvement comprises administering 0.75 mg of dulaglutide once weekly for a minimum of four weeks, then increasing the dose to 1.5 mg of dulaglutide once weekly for a minimum of four weeks, and then increasing the dose to 3.0 mg once weekly.

In another aspect, the present invention provides an improved method for administering dulaglutide to a subject having T2D and in need of further glycemic control, wherein the improvement comprises:
  a) administration of 3.0 mg of dulaglutide once weekly for a minimum of four weeks; and
  b) increasing the dose to 4.5 mg once weekly.

In another aspect, the present invention provides a method of providing chronic weight management to a subject in need thereof, comprising:
  a) administering to said subject 0.75 mg of dulaglutide once weekly for a minimum of four weeks;
  b) administering to said subject 1.5 mg of dulaglutide once weekly for a minimum of four weeks; and
  c) increasing the dose to 3.0 mg once weekly.

In another aspect, the present invention provides a method of providing chronic weight management to a subject in need thereof, comprising:
  a) identifying a subject who has been previously treated with 15 mg of dulaglutide once weekly for a minimum of four weeks; and
  b) increasing the dose to 3.0 mg once weekly.

In another aspect, the present invention provides a method of providing chronic weight management to a subject in need thereof, comprising:
  a) identifying a subject who has been previously treated with 3.0 mg of dulaglutide once weekly for a minimum of four weeks; and
  b) increasing the dose to 4.5 mg once weekly.

In another aspect, the present invention provides a stable pharmaceutical formulation comprising:
  a) dulaglutide, in a concentration selected from the group consisting of 6.0 or 9.0 mg/mL;
  b) mannitol, in a concentration of 46.4 mg/mL;
  c) trisodium citrate, in a concentration of 2.74 mg/mL; and
  d) polysorbate 80, in a concentration of 0.25 mg/mL.

In another aspect, the present invention provides dulaglutide for use in improving glycemic control in a subject having type 2 diabetes (T2D) and in need of additional glycemic control, comprising:
a) identifying a subject having T2D and in need of further glycemic control;
b) administering to said subject a first dose of dulaglutide once weekly for a minimum of four weeks; and
c) increasing the dose to a second dose,
wherein the first dose is selected from the group consisting of 1.5 and 3.0 mg once weekly, and the second dose is selected from the group consisting of 3.0 and 4.5 mg once weekly.

In another aspect, the present invention provides dulaglutide for use in improving glycemic control in a subject having type 2 diabetes (T2D) and in need of further glycemic control, comprising:
a) identifying a subject having T2D and in need of further glycemic control;
b) administering to said subject 0.75 mg of dulaglutide once weekly for a minimum of four weeks;
c) administering to said subject 1.5 mg of dulaglutide once weekly for a minimum of four weeks; and
d) administering to said subject 3.0 mg once weekly.

In another aspect, the present invention provides dulaglutide for use in improving glycemic control in a subject having type 2 diabetes (T2D) and being treated with a 1.5 mg dose of dulaglutide once weekly but in need of further glycemic control, comprising: increasing the dose of dulaglutide being administered to 3.0 mg once weekly.

In another aspect, the present invention provides dulaglutide for use in improving glycemic control in a subject having type 2 diabetes (T2D) and being treated with a 3.0 mg dose of dulaglutide once weekly but in need of further glycemic control, comprising: increasing the dose of dulaglutide being administered to 4.5 mg once weekly.

In another aspect, the present invention provides dulaglutide for use in providing chronic weight management to a subject in need thereof, comprising:
a) administering to said subject 0.75 mg of dulaglutide once weekly for a minimum of four weeks;
b) administering to said subject 1.5 mg of dulaglutide once weekly for a minimum of four weeks; and
c) increasing the dose to 3.0 mg once weekly.

In another aspect, the present invention provides dulaglutide for use in providing chronic weight management to a subject in need thereof, comprising:
a) identifying a subject who has been previously treated with 1.5 mg of dulaglutide once weekly for a minimum of four weeks; and
b) increasing the dose to 3.0 mg once weekly.

In another aspect, the present invention provides dulaglutide for use in providing chronic weight management to a subject in need thereof, comprising:
a) identifying a subject who has been previously treated with 3.0 mg of dulaglutide once weekly for a minimum of four weeks; and
b) increasing the dose to 4.5 mg once weekly.

In another aspect, the present invention provides use of dulaglutide for the manufacture of a medicament for improving glycemic control in a subject having type 2 diabetes (T2D) and in need of additional glycemic control, comprising:
a) identifying a subject having T2D and in need of further glycemic control;
b) administering to said subject a first dose of dulaglutide once weekly for a minimum of four weeks; and
c) increasing the dose to a second dose,
wherein the first dose is selected from the group consisting of 1.5 and 3.0 mg once weekly, and the second dose is selected from the group consisting of 3.0 and 4.5 mg once weekly.

In another aspect, the present invention provides use of dulaglutide for the manufacture of a medicament for improving glycemic control in a subject having type 2 diabetes (T2D) and in need of further glycemic control, comprising:
a) identifying a subject having T2D and in need of further glycemic control;
b) administering to said subject 0.75 mg of dulaglutide once weekly for a minimum of four weeks;
c) administering to said subject 1.5 mg of dulaglutide once weekly for a minimum of four weeks; and
d) administering to said subject 3.0 mg once weekly.

In another aspect, the present invention provides use of dulaglutide for the manufacture of a medicament for improving glycemic control in a subject having type 2 diabetes (T2D) and being treated with a 1.5 mg dose of dulaglutide once weekly but in need of further glycemic control, comprising: increasing the dose of dulaglutide being administered to 3.0 mg once weekly.

In another aspect, the present invention provides use of dulaglutide for the manufacture of a medicament for improving glycemic control in a subject having type 2 diabetes (T2D) and being treated with a 3.0 mg dose of dulaglutide once weekly but in need of further glycemic control, comprising: increasing the dose of dulaglutide being administered to 4.5 mg once weekly.

In another aspect, the present invention provides use of dulaglutide for the manufacture of a medicament for providing chronic weight management to a subject in need thereof, comprising:
a) administering to said subject 0.75 mg of dulaglutide once weekly for a minimum of four weeks;
b) administering to said subject 1.5 mg of dulaglutide once weekly for a minimum of four weeks; and
c) increasing the dose to 3.0 mg once weekly.

In another aspect, the present invention provides use of dulaglutide for the manufacture of a medicament for providing chronic weight management to a subject in need thereof, comprising:
a) identifying a subject who has been previously treated with 1.5 mg of dulaglutide once weekly for a minimum of four weeks; and
b) increasing the dose to 3.0 mg once weekly.

In another aspect, the present invention provides use of dulaglutide for the manufacture of a medicament for providing chronic weight management to a subject in need thereof, comprising:
a) identifying a subject who has been previously treated with 3.0 mg of dulaglutide once weekly for a minimum of four weeks; and
b) increasing the dose to 4.5 mg once weekly.

Dulaglutide is a human GLP-1 RA, which comprises a dimer of a GLP-1 analog fused at its C-terminus via a peptide linker to the N-terminus of an analog of an Fc portion of an immunoglobulin, and is identified by CAS registry number 923950-08-7. Each monomer of dulaglutide has the amino acid sequence set forth in SEQ ID NO:1:

```
                                                       (SEQ ID NO: 1)
           10        20        30        40        50        60
HGEGTFTSDVSSYLEEQAAKEFIAWLVKGGGGGGGSGGGGSGGGGSAESKYGPPCPPCPA 70        80        90       100       110       120
PEAAGGPSVFLFPPKPKDTLMISRTPEVTCVVVDVSQEDPEVQFNWYVDGVEVHNAKTKP 130       140       150       160       170       180
REEQFNSTYRVVSVLTVLHQDWLNGKEYKCKVSNKGLPSSIEKTISKAKGQPREPQVYTL 190       200       210       220       230       240
PPSQEEMTKNQVSLTCLVKGFYPSDIAVEWESNGQPENNYKTTPPVLDSDGSFFLYSRLT 250       260       270
VDKSRWQEGNVFSCSVMHEALHNHYTQKSLSLSLG.
```

The two monomers are attached by disulfide bonds to form the dimer. Dulaglutide's structure, function, production and use in treating T2D is described in more detail in U.S. Pat. No. 7,452,966 and U.S. Patent Application Publication No. US20100196405. When used herein, the term "dulaglutide" refers to any GLP-1 RA protein dimer of two monomers having the amino acid sequence of SEQ ID NO:1, including any protein that is the subject of a regulatory submission seeking approval of a GLP-1 RA product which relies in whole or part upon data submitted to a regulatory agency by Eli Lilly and Company relating to dulaglutide, regardless of whether the party seeking approval of said protein actually identifies the protein as dulaglutide or uses some other term.

Dulaglutide stimulates insulin synthesis and secretion, and has been shown to provide improved glycemic control in T2D patients as compared to placebo, both when administered in combination with metformin. As noted above, dulaglutide 0.75 mg and 1.5 mg doses were selected for Phase 3 registration studies, were submitted for regulatory approval, were approved in 2014 and have been used to provide glycemic control in thousands of T2D patients since that time. As also noted above, however, many T2D patients worldwide continue to fail to reach their HbA1c goals and struggle with weight management, so new therapies capable of providing additional glycemic control and/or weight loss are needed.

Although increasing the dose of a drug may, in some cases, be capable of achieving increased efficacy, increasing the dose of a drug also carries a risk of greater side effects. For example, administration of GLP-1 RAs is known to run the risk of nausea, diarrhea and vomiting (see, e.g., TRULICITY® Prescribing Information), and in 33 patients treated with 3.0 mg or higher doses of dulaglutide in a Phase 1 dosing study and in the dose-finding portion of a Phase 2/3 study, the incidence of gastrointestinal (GI) adverse events (AEs) that are commonly related to the treatment with GLP-1 RAs—e.g., nausea (17 patients, 52%) and vomiting (9 patients, 27%)—was higher than the incidence reported with the currently approved doses in Phase 3 registration trials (see, e.g., Barrington et al. A 5-week study of the pharmacokinetics and pharmacodynamics of LY2189265, a novel, long-acting glucagon-like peptide-1 analogue, in patients with type 2 diabetes. *Diabetes ObesMetab.* 2011; 13(5):426-433; Skrivanek et al. Dose-finding results in an adaptive, seamless, randomized trial of once-weekly dulaglutide combined with metformin in type 2 diabetes patients (AWARD-5). *Diabetes Obes. Metab.* 2014; 16(8):748-756); Jendle et al Efficacy and safety of dulaglutide in the treatment of type 2 diabetes: a comprehensive review of the dulaglutide clinical data focusing on the AWARD phase 3 clinical trial program. *Diabetes Metab Res Rev.* 2016; 32(8): 776-790). Five out of the 33 patients (15%) actually discontinued treatment early due to GI AEs. In addition to GI tolerability issues, earlier studies on higher doses had also suggested that an increase in dose could also carry the risk of causing an unacceptable increase in heart rate (see, e.g., Skrivanek 2014). Indeed, following a number of unblinded interim data reviews in one of the studies referenced above, which initially included seven doses in the range of 0.25 mg to 3.0 mg, the Data Monitoring Committee (DMC) recommended discontinuing randomization of patients to the dulaglutide 3.0 mg dose because of higher incidence in pancreatic enzyme values above upper limit of normal (ULN), increases in heart rate (HR), and higher incidence of GI adverse events (see, e.g., Skrivanek 2014). Thus, any increase in dose must strike a balance between sufficiently enhanced efficacy while not leading to unacceptable safety or tolerability issues.

It has been discovered that increased doses of 3.0 mg or 4.5 mg dulaglutide once weekly are capable of providing enhanced efficacy as compared to the currently available 0.75 mg and 1.5 mg doses, and may be administered with acceptable safety and tolerability profiles if an upward dose titration regimen is used prior to their administration. Thus, the present invention provides for administering dulaglutide doses of 3.0 mg and 4.5 mg once weekly, as well as a dose titration regimen that results in an acceptable safety and tolerability profile when administering the 3.0 mg and 4.5 mg doses. In subjects for whom dulaglutide treatment is first being initiated, the dose titration regimen includes initiating treatment with a 0.75 mg dose once weekly, then raising the dose to 1.5 mg once weekly, then raising the dose to 3.0 mg once weekly, then, optionally, raising the dose to 4.5 mg once weekly. In subjects for whom dulaglutide is already being administered but in need of further glycemic control, however, the dose titration regimen does not require decreasing the subject's current dose. For example, in a subject who has been receiving 1.5 mg dulaglutide once weekly but in need of further glycemic control, the regimen does not require decreasing the dose to 0.75 mg, but instead constitutes increasing the dose to 3.0 mg, and then, optionally, to 4.5 mg. Likewise, in a subject who has been receiving 3.0 mg dulaglutide once weekly but in need of further glycemic control, the regimen does not require decreasing the dose to 0.75 mg or 1.5 mg once weekly, but instead constitutes increasing the dose to 4.5 mg. For any of the above-described embodiments of the dose titration regimen, however, the dose is preferably not increased to the next succeeding dose in the progression until the current dose has been administered for a minimum of four weeks.

It was also discovered, however, that increasing the dulaglutide concentration also requires other modifications to the current commercial formulations, so the present invention also provides for new formulations which ensure that compositions containing the increased doses of dulaglutide will remain chemically and physically stable—and meet the current product specifications—throughout the 2 year refrigerated shelf-life and 14 day in use period.

The currently approved products containing dulaglutide are provided in 0.5 mL aqueous solutions containing either 0.75 mg or 1.5 mg of dulaglutide as well as the following excipients: citric acid anhydrous (0.07 mg), mannitol (23.2 mg), polysorbate 80 (PS80) (0.10 mg), and trisodium citrate dihydrate (1.37 mg) (TRULICITY® Highlights of Prescribing Information). PS80 is provided in the formulation in order to help provide protection against physical stress and ensure the dulaglutide protein remains physically stable for the duration of the product shelf-life, 2 years under refrigerated conditions, and maximum in use period, up to 14 days at room temperature. The dulaglutide product specification thus includes a lower limit for PS80 concentration above which the concentration of PS80 must remain throughout the duration of the shelf-life and in use period. In order to ensure the concentration of PS80 remains above that lower specification limit for the duration of the shelf-life and in use period, the currently approved dulaglutide products contain a PS80 concentration of 0.1 mg/0.5 mL (0.02% w/v) when manufactured.

When the concentration of dulaglutide is increased to the higher doses provided in the methods of the current invention, the concentration of PS80 decreases further than in the currently approved formulations due to increased hydrolysis, and changes to the formulation were needed to ensure sufficient PS80 is present to meet product specifications and provide physical stability. As described in more detail in the Examples below, it was determined that increasing the concentration of PS80 to 0.025% would ensure the PS80 specification limit could be met throughout shelf-life and in-use with the higher dulaglutide doses provided in the methods of the present invention, but would not be so high as to generate unacceptable visible particulates resulting from hydrolysis of PS80, or otherwise have any undesired effects on the chemical or physical stability of the formulations. Thus, in certain embodiments, the methods of the present invention are performed by administering the increased doses of dulaglutide in 0.5 mL aqueous solutions containing 3.0 mg or 4.5 mg of dulaglutide, citric acid anhydrous (0.07 mg), mannitol (23.2 mg), trisodium citrate dihydrate (1.37 mg) and polysorbate 80 (PS80) (0.125 mg). In certain embodiments, the methods of the present invention are performed by administering the increased doses of dulaglutide in solutions of any volume containing 6.0 mg or 9.0 mg/mL of dulaglutide, 0.14 mg/mL citric acid anhydrous, 46.4 mg/mL mannitol, 2.74 mg/mL trisodium citrate dehydrate and 0.25 mg/mL polysorbate 80 (PS80).

When used herein, the terms "treatment," "treat," "treating," and the like, are meant to include slowing or attenuating the progression of a disease or disorder. These terms also include alleviating, ameliorating, attenuating, eliminating, or reducing one or more symptoms of a disorder or condition, even if the disorder or condition is not actually eliminated and even if progression of the disorder or condition is not itself slowed or reversed.

A "subject" refers to a mammal, preferably a human with a disease, disorder or condition that would benefit from treatment with an increased dose of dulaglutide.

"Glycemic control" refers to the maintenance or reduction of a subject's HbA1c levels; "improv[ing]" glycemic control refers to reductions in HbA1c; and "in need of further" glycemic control refers to a need for reductions in HbA1c.

"Chronic weight management" refers to a reduction in body weight.

"HbA1c" refers to glycated hemoglobin levels, which develop when hemoglobin joins with glucose in the blood. HbA1c levels are a commonly used measure of glycemic control in patients with diabetes, with decreased HbA1c levels generally indicating improved glycemic control. In the context of the methods of the present invention, the methods of the present invention result in a decrease in HbA1c. In certain embodiments, the decrease in HbA1c is decreased relative to the HbA1c levels resulting from treatment with the currently approved 0.75 mg and 1.5 mg dulaglutide doses.

In certain embodiments of the present invention, the dulaglutide doses and dosing regimens described herein are provided for the treatment of obesity, chronic weight management and/or non-therapeutic weight loss in subjects in need thereof. In certain embodiments, the subject has a body mass index (BMI) of greater than about 25 $kg/m^2$. In certain embodiments, the subject has a body mass index (BMI) of greater than about 26 $kg/m^2$. In certain embodiments, the subjects has a body mass index (BMI) of greater than about 27 $kg/m^2$. In certain embodiments, the subject also has one or more weight-related comorbid conditions such as T2D, hypertension and/or dyslipidemia.

In certain embodiments, the doses and dosing regimens described herein are provided for the treatment of other diseases or conditions such as fatty liver disease (FLD), non-alcoholic steatohepatitis (NASH) or chronic kidney disease (CKD).

In certain embodiments, the dulaglutide doses and dosing regimens described herein are provided for the prevention and/or treatment of cognitive disorders and/or neurodegenerative disorders, such as Alzheimer's disease, Parkinson's disease, and/or multiple sclerosis.

The methods of treatment and uses described herein may be provided in simultaneous or sequential combination with other T2D treatments, including oral T2D medications such as metformin, and/or other injectable medications including rapid-acting or basal insulins.

Additional embodiments of the present invention are described below:

1. A method of improving glycemic control in a subject having type 2 diabetes (T2D) comprising administering to said subject an increased dose of dulaglutide once weekly, wherein the increased dose is selected from the group consisting of 3.0 mg and 4.5 mg dulaglutide once weekly.

2. A method of improving glycemic control in a subject having type 2 diabetes (T2D) and in need of further glycemic control, comprising:
   a) administering to said subject 1.5 mg of dulaglutide once weekly; and
   b) administering to said subject an increased dose of dulaglutide once weekly wherein the increased dose is selected from the group consisting of 3.0 and 4.5 mg dulaglutide once weekly.

3. A method of improving glycemic control in a subject having type 2 diabetes (T2D), comprising:
   a) administering to said subject 0.75 mg of dulaglutide once weekly; followed by
   b) administering to said subject 1.5 mg of dulaglutide once weekly; followed by
   c) administering to said subject an increased dose of dulaglutide once weekly.

4. A method of improving glycemic control in a subject having type 2 diabetes (T2D) and in need of further glycemic control, comprising:

a) identifying a subject who has been previously treated with 1.5 mg of dulaglutide once weekly; followed by
b) administering an increased dose of dulaglutide once weekly.

5. The method of any of embodiments 1-4 wherein the 1.5 mg of dulaglutide once weekly is administered for two or more weeks before administering the increased dose of dulaglutide.

6. The method of any of embodiments 1-5 wherein the 1.5 mg of dulaglutide once weekly is administered for a minimum of four weeks before administering the increased dose of dulaglutide.

7. An improved method for administering dulaglutide to a subject having (T2D) in need of further glycemic control, wherein the improvement comprises administration of an increased dose of dulaglutide selected from the group consisting of 3.0 mg and 4.5 mg once weekly.

8. A method of improving glycemic control in a subject having type 2 diabetes (T2D) and in need of further glycemic control, comprising:
a) administering to said subject 3.0 mg of dulaglutide once weekly; followed by
b) administering to said subject 4.5 mg of dulaglutide once weekly.

9. A method of improving glycemic control in a subject having type 2 diabetes (T2D), comprising:
a) administering to said subject 1.5 mg of dulaglutide once weekly; followed by
b) administering to said subject 3.0 mg of dulaglutide once weekly; followed by
c) administering to said subject 4.5 mg of dulaglutide once weekly.

10. A method of improving glycemic control in a subject having type 2 diabetes (T2D) and in need of further glycemic control, comprising:
a) administering to said subject 0.75 mg of dulaglutide once weekly; followed by
b) administering to said subject 1.5 mg of dulaglutide once weekly; followed by
c) administering to said subject 3.0 mg of dulaglutide once weekly; followed by
d) administering to said subject 4.5 mg of dulaglutide once weekly.

11. A method of improving glycemic control in a subject having type 2 diabetes (T2D) and in need of further glycemic control, comprising:
a) identifying a subject who has been previously treated with 3.0 mg of dulaglutide once weekly; followed by
b) administering 4.5 mg of dulaglutide once weekly.

12. The method of any of the above embodiments wherein each dose of dulaglutide once weekly is administered for two or more weeks before administering the increased dose of dulaglutide.

13. The method of any of the above embodiments wherein each identified dose of dulaglutide is administered for a minimum of four weeks before administering the subsequent increased dose of dulaglutide.

14. An improved method for administering dulaglutide to a subject having (T2D) who is being administered a first dose of dulaglutide but who is in need of further glycemic control, wherein the improvement comprises administration of an increased dose of dulaglutide.

15. The improved method of embodiment 14 wherein the first dose of dulaglutide 1.5 mg and the second dose of dulaglutide is 3.0 mg.

16. The improved method of any of embodiments 14-15 wherein the first dose of dulaglutide has been administered for two or more weeks before administering the second dose of dulaglutide.

17. The improved method of any of embodiments 14-15 wherein the first dose of dulaglutide has been administered for a minimum of four weeks before administering the second dose of dulaglutide.

18. The method of any of the above embodiments wherein the method results in a decrease in HbA1c.

19. The method of any of the above embodiments wherein the method results in a decrease in HbA1c of greater than about 0.1% as compared to treatment with 1.5 mg dulaglutide once weekly.

20. The method of any of the above embodiments wherein the method results in a decrease in HbA1c of greater than about 0.2% as compared to treatment with 1.5 mg dulaglutide once weekly.

21. The method of any of the above embodiments wherein the method results in a decrease in HbA1c of greater than about 0.3% as compared to treatment with 1.5 mg dulaglutide once weekly.

22. The method of any of the above embodiments wherein the method results in a decrease in HbA1c of greater than about 0.5% as compared to treatment with 1.5 mg dulaglutide once weekly.

23. A method of providing chronic weight management to a subject in need thereof comprising administering to said subject dulaglutide in amounts according to any of the above embodiments.

24. The method of any of the above embodiments wherein the method results in a decrease in body weight.

25. The method of any of the above embodiments wherein the method results in a decrease in body weight of at least about 1 kg as compared to treatment with 1.5 mg dulaglutide once weekly.

26. The method of any of the above embodiments wherein the method results in a decrease in body weight of at least about 1.3 kg as compared to treatment with 1.5 mg dulaglutide once weekly.

27. The method of any of the above embodiments wherein the method results in a decrease in body weight of at least about 1.5 kg as compared to treatment with 1.5 mg dulaglutide once weekly.

28. The method of any of the above embodiments wherein the method results in a decrease in body weight of at least about 2 kg as compared to treatment with 1.5 mg dulaglutide once weekly.

29. A method of treating NASH in a subject in need thereof comprising administering to said subject dulaglutide in amounts according to any of the above embodiments.

30. A method of treating metabolic disease in a subject in need thereof comprising administering to said subject dulaglutide in amounts according to any of the above embodiments.

31. A method of treating CKD in a subject in need thereof comprising administering to said subject dulaglutide in amounts according to any of the above embodiments.

32. A method of treating Alzheimer's disease in a subject in need thereof comprising administering to said subject dulaglutide in amounts according to any of the above embodiments.

33. A method of treating Parkinson's disease in a subject in need thereof comprising administering to said subject dulaglutide in amounts according to any of the above embodiments.

34. A method of treating multiple sclerosis in a subject in need thereof comprising administering to said subject dulaglutide in amounts according to any of the above embodiments.

35. The method of any of the above embodiments, wherein the administration dulaglutide does not result in unacceptable GI tolerability.

36. The method of any of the above embodiments, wherein the administration of dulaglutide does not result in an unacceptable increase in pulse rate.

37. The method of any of the above embodiments, wherein the increased dose of dulaglutide is administered in a 0.5 mL aqueous composition comprising:
   a) 0.07 mg citric acid;
   b) 23.2 mg mannitol;
   c) 1.37 mg trisodium citrate; and
   d) between about 0.125-about 0.25 mg polysorbate 80.

38. The method of embodiment 37 wherein the amount of polysorbate 80 in the composition is about 0.125 mg.

39. The method of either of embodiments 37-38, wherein the composition remains chemically and physically stable for 2 years at 2-8° C.

40. The method of any of embodiments 37-39, wherein the composition remains chemically and physically stable for 14 days at 30° C.

41. A stable pharmaceutical composition comprising:
   a) dulaglutide, in a concentration selected from the group consisting of 6.0 or 9.0 mg/mL;
   b) mannitol, in a concentration of 46.4 mg/mL;
   c) trisodium citrate, in a concentration of 2.74 mg/mL; and
   d) polysorbate 80, in a concentration between about 0.25 and 0.5 mg/mL.

42. The stable pharmaceutical composition of embodiment 41, wherein the concentration of polysorbate 80 is about 0.25 mg/mL.

43. The stable pharmaceutical composition of either of embodiments 41 or 42, wherein the concentration of dulaglutide is 6.0 mg/mL.

44. The stable pharmaceutical composition of either of embodiments 41 or 42, wherein the concentration of dulaglutide is 9.0 mg/mL.

45. The stable pharmaceutical composition of either of embodiments 41 or 42, wherein the composition remains chemically and physically stable for 2 years at 2-8° C.

46. The stable pharmaceutical composition of any of embodiments 41, 42 or 45, wherein the composition remains chemically and physically stable for 14 days at 30° C.

47. An autoinjector comprising the stable pharmaceutical composition of any of embodiments 41-46.

48. A method of improving glycemic control in a subject having type 2 diabetes (T2D) comprising administering to said subject 0.5 mL of the stable pharmaceutical composition of any of embodiments 41-44.

49. Dulaglutide for use in improving glycemic control in a subject having type 2 diabetes (T2D) and in need of additional glycemic control, comprising:
   a) identifying a subject having T2D and in need of further glycemic control;
   b) administering to said subject a first dose of dulaglutide once weekly for a minimum of four weeks; and
   c) increasing the dose to a second dose,
wherein the first dose is selected from the group consisting of 1.5 and 3.0 mg once weekly, and the second dose is selected from the group consisting of 3.0 and 4.5 mg once weekly.

50. Dulaglutide for use according to embodiment 49, wherein the first dose is 1.5 mg and the second dose is 3.0 mg.

51. Dulaglutide for use according to embodiment 49, wherein the subject had been treated with a 0.75 mg dose of dulaglutide for a minimum of four weeks before administering the 1.5 mg dose.

52. Dulaglutide for use according to either of embodiments 50 or 51, further comprising increasing the 3.0 mg dose to 4.5 mg once weekly after the subject has been treated with the 3.0 mg dose for a minimum of four weeks.

53. Dulaglutide for use according to embodiment 49, wherein the first dose is 3.0 mg and the second dose is 4.5 mg.

54. Use of dulaglutide for the manufacture of a medicament for improving glycemic control in a subject having type 2 diabetes (T2D) and in need of additional glycemic control, comprising:
   a) identifying a subject having T2D and in need of further glycemic control;
   b) administering to said subject a first dose of dulaglutide once weekly for a minimum of four weeks; and
   c) increasing the dose to a second dose,
wherein the first dose is selected from the group consisting of 1.5 and 3.0 mg once weekly, and the second dose is selected from the group consisting of 3.0 and 4.5 mg once weekly.

55. The use of embodiment 54 wherein the first dose is 1.5 mg and the second dose is 3.0 mg.

56. The use embodiment 55, wherein the subject had been treated with a 0.75 mg dose of dulaglutide for a minimum of four weeks before administering the 1.5 mg dose.

57. The use of any of embodiments 54-56, further comprising increasing the 3.0 mg dose to 4.5 mg once weekly after the subject has been treated with the 3.0 mg dose for a minimum of four weeks.

58. The use of embodiment 54 wherein the first dose is 3.0 mg and the second dose is 4.5 mg.

59. Dulaglutide for use in improving glycemic control in a subject having type 2 diabetes (T2D) and in need of further glycemic control, comprising:
   a) identifying a subject having T2D and in need of further glycemic control;
   b) administering to said subject 0.75 mg of dulaglutide once weekly for a minimum of four weeks;
   c) administering to said subject 1.5 mg of dulaglutide once weekly for a minimum of four weeks; and
   d) administering to said subject 3.0 mg once weekly.

60. Dulaglutide for use according to embodiment 59, further comprising increasing the dose to 4.5 mg once weekly after the subject has been administered the 3.0 mg dose once weekly for a minimum of four weeks.

61. Use of dulaglutide for the manufacture of a medicament for improving glycemic control in a subject having type 2 diabetes (T2D) and in need of further glycemic control, comprising:
   a) identifying a subject having T2D and in need of further glycemic control;
   b) administering to said subject 0.75 mg of dulaglutide once weekly for a minimum of four weeks;
   c) administering to said subject 1.5 mg of dulaglutide once weekly for a minimum of four weeks; and
   d) administering to said subject 3.0 mg once weekly.

62. The use of embodiment 61, further comprising increasing the dose to 4.5 mg once weekly after the subject has been administered the 3.0 mg dose once weekly for a minimum of four weeks.

63. Dulaglutide for use in improving glycemic control in a subject having type 2 diabetes (T2D) and being treated with a 1.5 mg dose of dulaglutide once weekly but in need of further glycemic control, comprising: increasing the dose of dulaglutide being administered to 3.0 mg once weekly.

64. Dulaglutide for use according to embodiment 61, further comprising increasing the dose to 4.5 mg once weekly after the subject has been administered the 3.0 mg dose once weekly for a minimum of four weeks.

65. Use of dulaglutide for the manufacture of a medicament for improving glycemic control in a subject having type 2 diabetes (T2D) and being treated with a 1.5 mg dose of dulaglutide once weekly but in need of further glycemic control, comprising: increasing the dose of dulaglutide being administered to 3.0 mg once weekly.

66. The use of embodiment 65, further compring increasing the dose to 4.5 mg once weekly after the subject has been treated with 3.0 mg dulaglutide once weekly for a minimum of four weeks.

67. Dulaglutide for use in improving glycemic control in a subject having type 2 diabetes (T2D) and being treated with a 3.0 mg dose of dulaglutide once weekly but in need of further glycemic control, comprising: increasing the dose of dulaglutide being administered to 4.5 mg once weekly.

68. Dulaglutide for use in providing chronic weight management to a subject in need thereof, comprising:
   a) administering to said subject 0.75 mg of dulaglutide once weekly for a minimum of four weeks;
   b) administering to said subject 1.5 mg of dulaglutide once weekly for a minimum of four weeks; and
   c) increasing the dose to 3.0 mg once weekly.

69. Dulaglutide for use according to embodiment 68, further comprising increasing the dose to 4.5 mg once weekly after the subject has been administered the 3.0 mg dose once weekly for a minimum of four weeks.

70. Dulaglutide for use in providing chronic weight management to a subject in need thereof, comprising:
   a) identifying a subject who has been previously treated with 1.5 mg of dulaglutide once weekly for a minimum of four weeks; and
   b) increasing the dose to 3.0 mg once weekly.

71. Dulaglutide for use according to embodiment 70, further comprising increasing the dose to 4.5 mg once weekly after the subject has been administered the 3.0 mg dose once weekly for a minimum of four weeks.

72. Dulaglutide for use in providing chronic weight management to a subject in need thereof, comprising:
   a) identifying a subject who has been previously treated with 3.0 mg of dulaglutide once weekly for a minimum of four weeks; and
   b) increasing the dose to 4.5 mg once weekly.

73. Use of dulaglutide for the manufacture of a medicament for improving glycemic control in a subject having type 2 diabetes (T2D) and being treated with a 3.0 mg dose of dulaglutide once weekly but in need of further glycemic control, comprising: increasing the dose of dulaglutide being administered to 4.5 mg once weekly.

74. Use of dulaglutide for the manufacture of a medicament for providing chronic weight management to a subject in need thereof, comprising:
   a) administering to said subject 0.75 mg of dulaglutide once weekly for a minimum of four weeks;
   b) administering to said subject 1.5 mg of dulaglutide once weekly for a minimum of four weeks; and
   c) increasing the dose to 3.0 mg once weekly.

75. The use of embodiment 74, further comprising increasing the dose to 4.5 mg once weekly after the subject has been treated with 3.0 mg dulaglutide once weekly for a minimum of four weeks.

76. Use of dulaglutide for the manufacture of a medicament for providing chronic weight management to a subject in need thereof, comprising:
   a) identifying a subject who has been previously treated with 1.5 mg of dulaglutide once weekly for a minimum of four weeks; and
   b) increasing the dose to 3.0 mg once weekly.

77. The use of embodiment 76, further comprising increasing the dose to 4.5 mg once weekly after the subject has been treated with 3.0 mg dulaglutide once weekly for a minimum of four weeks.

78. Use of dulaglutide for the manufacture of a medicament for providing chronic weight management to a subject in need thereof, comprising:
   a) identifying a subject who has been previously treated with 3.0 mg of dulaglutide once weekly for a minimum of four weeks; and
   b) increasing the dose to 4.5 mg once weekly.

79. Dulaglutide for use according to any of the above embodiments, wherein the 3.0 mg or 4.5 mg dose of dulaglutide is administered in a 0.5 mL aqueous composition comprising:
   a) 0.07 mg citric acid;
   b) 23.2 mg mannitol;
   c) 1.37 mg trisodium citrate; and
   d) polysorbate 80 in an amount between 0.125 and 0.25 mg.

80. Dulaglutide for use according to embodiment 79 wherein the polysorbate amount is 0.125 mg.

81. Dulaglutide for use according to any of embodiments 79-80, wherein the composition remains chemically and physically stable for 24 months at 2-8° C.

82. Dulaglutide for use according to any of embodiments 79-81, wherein the composition remains chemically and physically stable for 14 days at 30° C.

83. Dulaglutide for use according to any of the above embodiments, wherein administration of the increased dose of dulaglutide does not result in unacceptable tolerability.

84. Dulaglutide for use in any of the above embodiments, wherein the subject's HbA1c is lowered.

85. Dulaglutide for use in any of the above embodiments, wherein the subject's body weight decreases.

The invention is further illustrated by the following examples, which are not to be construed as limiting.

EXAMPLES

Phase 2 Clinical Study.

A Phase 2 clinical trial is designed to assess the safety and efficacy of once weekly dulaglutide 3.0 mg and 4.5 mg, administered following one of two dose titration algorithms, in comparison to placebo in patients with type 2 diabetes mellitus (T2D) treated with metformin monotherapy. The trial is also designed to include exploratory comparisons of 3.0 and 4.5 mg doses to dulaglutide 1.5 mg (the highest dose approved by regulatory agencies). The trial is intended to predict whether the increased doses will provide improved clinical benefits, including greater reduction in HbA1c and greater body weight reduction, with an acceptable safety and tolerability profile.

The study is designed as a multicenter, randomized, double-blind, parallel-arm, placebo-controlled trial with 3 study periods (lead-in, treatment, and safety follow-up) in patients who have T2D with inadequate glycemic control on metformin only.

After screening and a lead-in period, patients are randomized in a 1:1:1:1 ratio to weekly injections of dulaglutide 4.5 mg, 3.0 mg, or 1.5 mg, or placebo, in combination with stable doses of metformin. Within each of the investigational dulaglutide dose (3.0 mg and 4.5 mg) arms, patients are randomly assigned in a 1:1 ratio to one of two dulaglutide dose titration algorithms and participants are treated for 18 weeks after randomization in a double-blind manner, comprising 6 weeks of a titration phase and a 12 week maintenance treatment phase at the final dose. During the titration phase in the 3.0 and 4.5 mg arms, the dose of dulaglutide is escalated over 6 weeks according to one of two algorithms: (1) patients receive dulaglutide 1.5 mg once weekly for the first 4 weeks (Weeks 1-4) followed by dulaglutide 3.0 mg once weekly for the next 2 weeks (Weeks 5-6) (hereafter, "Algorithm 1" or "A1"); or (2) patients received dulaglutide 0.75 mg once weekly for the first 2 weeks (Weeks 1-2) followed by dulaglutide 1.5 mg once weekly for the next 4 weeks (Weeks 3-6) (hereafter, "Algorithm 2" or "A2"). The 2 titration algorithms are chosen based on modeling and simulations including data from several Phase 2 and Phase 3 trials to assess the potential mitigating effect of doubling increases in titrated doses (i.e., Algorithm 1) versus longer exposure at lower titration doses (i.e., Algorithm 2).

A total of 505 patients are screened and 318 patients were randomized to treatment: placebo, 82; dulaglutide 1.5 mg, 81; dulaglutide 3.0 mg, 79; dulaglutide 4.5 mg, 76. One patient randomized to placebo withdrew consent to participate in the study at Visit 4 and did not receive any doses of study drug, so 317 patients received at least 1 dose of study drug and comprised the intent-to-treat (ITT) Population: placebo, 81; dulaglutide 1.5 mg, 81; dulaglutide 3.0 mg, 79; dulaglutide 4.5 mg, 76.

A summary of the changes from baseline in HbA1c (%) and body weight (kg) at Week 18 in the ITT population, excluding data collected post-rescue (patients that had high blood glucose requiring rescue with another therapy) and post study drug discontinuation is provided below in Table 1. The HbA1c data also excludes results for patients demonstrating large, unexplained swings in HbA1c considered to be physiologically implausible and not consistent with the other clinical information available.

TABLE 1

Change in HbA1c (%) and body weight (kg) at Week 18, ITT population excluding post rescue or study drug discontinuation data.

| | LS Mean Change from Baseline (SE) [n] | | | | LS Mean Differences (95% CI) | | |
|---|---|---|---|---|---|---|---|
| Parameter | PBO | Dula 1.5 | Dula 3.0 | Dula 4.5 | Dula 1.5-PBO | Dula 3.0-Dula 1.5 | Dula 4.5-Dula 1.5 |
| Change in HbA1c (%) | −0.42 (0.097) [66] | −1.24** (0.094) [72] | −1.47** (0.097) [67] | −1.50** (0.101) [58] | −0.82** (−1.08, −0.56) | −0.22 (−0.48, 0.03) | −0.26 (−0.52, 0.00) |
| Change in body weight (kg) | −1.6 (0.41) [66] | −2.9* (0.40) [71] | −4.2**† (0.41) [68] | −4.4**† (0.43) [59] | −1.3* (−2.4, −0.2) | −1.3† (−2.4, −0.2) | −1.5† (−2.6, −0.3) |

Abbreviations: CI = confidence interval; LS mean = least-squares mean; PBO = placebo.
*P-value for comparison of dulaglutide vs. placebo <0.05.
**P-value for comparison of dulaglutide vs. placebo <0.001.
†P-value for comparison of dulaglutide vs. dulaglutide 1.5 mg <0.05.
Notes:
Dula X.X represents X.X milligrams of dulaglutide administered once weekly.

At week 18, all three doses of dulaglutide reduced HbA1c significantly from baseline compared to placebo and significantly reduced body weight from baseline compared to placebo. HbA1c declined by a mean of −1.24% in the dulaglutide 1.5 mg group, compared with −1.47% in the dulaglutide 3.0 mg group (LS mean treatment difference, −0.22%; 95% CI−0.48%, 0.03%) and −1.50% in the dulaglutide 4.5 mg group (LS mean treatment difference, −0.26%; 95% CI−0.52%, 0.00%). Body weight declined by a mean of −2.9 kg in the dulaglutide 1.5 mg group, compared with −4.2 kg in the dulaglutide 3.0 mg group (LS mean treatment difference, −1.3 kg; 95% CI−2.4, 0.2) and −4.4 kg in the dulaglutide 4.5 mg group (LS mean treatment difference, −1.5 kg; 95% CI−2.6, −0.3). The incremental efficacy on HbA1c reduction of both higher doses relative to dulaglutide 1.5 mg was greater in subgroups of patients with higher baseline HbA1c levels.

Table 2 summarizes frequency of nausea, vomiting, and diarrhea by treatment, as measured by prevalence (any patient who had a new or ongoing event during the interval), incidence (any patient who had an event begin during the interval), and first onset (any patient who had the first event of that type during the interval) of the events over 3 time periods (Weeks 0-6 [titration period], Weeks 6-10 [first 4 weeks after completion of titration for patients in the dulaglutide 3.0 mg and dulaglutide 4.5 mg groups], and Weeks 0-18 [treatment period]).

TABLE 2

Summary of Prevalence, Incidence, and First Onset of Nausea, Vomiting, and Diarrhea by Treatment and Time Period, Intent-to-Treat Population.

| Event/<br>Parameter/<br>Time Period | Placebo<br>(N = 81)<br>m/M (%) | Dula 1.5<br>(N = 81)<br>m/M (%) | Dula 3.0<br>(N = 79)<br>m/M (%) | Dula 4.5<br>(N = 76)<br>m/M (%) |
|---|---|---|---|---|
| Nausea | | | | |
| Prevalence | | | | |
| Wks 0-6 | 3/81 (3.7) | 16/81 (19.8) | 16/79 (20.3) | 17/76 (22.4) |
| Wks 6-10 | 1/81 (1.2) | 9/81 (11.1) | 8/78 (10.3) | 14/75 (18.7) |
| Wks 0-18 | 4/81 (4.9) | 18/81 (22.2) | 19/79 (24.1) | 23/76 (30.3) |
| Incidence | | | | |
| Wks 0-6 | 3/81 (3.7) | 16/81 (19.8) | 16/79 (20.3) | 17/76 (22.4) |
| Wks 6-10 | 1/81 (1.2) | 6/81 (7.4) | 5/78 (6.4) | 10/75 (13.3) |
| Wks 0-18 | 4/81 (4.9) | 18/81 (22.2) | 19/79 (24.1) | 23/76 (30.3) |
| Onset | | | | |
| Wks 0-6 | 3/81 (3.7) | 16/81 (19.8) | 16/79 (20.3) | 17/76 (22.4) |
| Wks 6-10 | 1/81 (1.2) | 2/81 (2.5) | 3/78 (3.8) | 5/75 (6.7) |
| Wks 0-18 | 4/81 (4.9) | 18/81 (22.2) | 19/79 (24.1) | 23/76 (30.3) |
| Vomiting | | | | |
| Prevalence | | | | |
| Wks 0-6 | 2/81 (2.5) | 7/81 (8.6) | 7/79 (8.9) | 5/76 (6.6) |
| Wks 6-10 | 3/81 (3.7) | 2/81 (2.5) | 2/78 (2.6) | 4/75 (5.3) |
| Wks 0-18 | 4/81 (4.9) | 9/81 (11.1) | 8/79 (10.1) | 10/76 (13.2) |
| Incidence | | | | |
| Wks 0-6 | 2/81 (2.5) | 7/81 (8.6) | 7/79 (8.9) | 5/76 (6.6) |
| Wks 6-10 | 2/81 (2.5) | 2/81 (2.5) | 2/78 (2.6) | 3/75 (4.0) |
| Wks 0-18 | 4/81 (4.9) | 9/81 (11.1) | 8/79 (10.1) | 10/76 (13.2) |
| Onset | | | | |
| Wks 0-6 | 2/81 (2.5) | 7/81 (8.6) | 7/79 (8.9) | 5/76 (6.6) |
| Wks 6-10 | 2/81 (2.5) | 2/81 (2.5) | 1/78 (1.3) | 3/75 (4.0) |
| Wks 0-18 | 4/81 (4.9) | 9/81 (11.1) | 8/79 (10.1) | 10/76 (13.2) |
| Diarrhea | | | | |
| Prevalence | | | | |
| Wks 0-6 | 5/81 (6.2) | 6/81 (7.4) | 11/79 (13.9) | 9/76 (11.8) |
| Wks 6-10 | 2/81 (2.5) | 4/81 (4.9) | 10/78 (12.8) | 9/75 (12.0) |
| Wks 0-18 | 9/81 (11.1) | 9/81 (11.1) | 19/79 (24.1) | 15/76 (19.7) |
| Incidence | | | | |
| Wks 0-6 | 5/81 (6.2) | 6/81 (7.4) | 11/79 (13.9) | 9/76 (11.8) |
| Wks 6-10 | 1/81 (1.2) | 3/81 (3.7) | 5/78 (6.4) | 7/75 (9.3) |
| Wks 0-18 | 9/81 (11.1) | 9/81 (11.1) | 19/79 (24.1) | 15/76 (19.7) |
| Onset | | | | |
| Wks 0-6 | 5/81 (6.2) | 6/81 (7.4) | 11/79 (13.9) | 9/76 (11.8) |
| Wks 6-10 | 1/81 (1.2) | 2/81 (2.5) | 5/78 (6.4) | 5/75 (6.7) |
| Wks 0-18 | 9/81 (11.1) | 9/81 (11.1) | 19/79 (24.1) | 15/76 (19.7) |

Abbreviations:
m = number of patients with event during the interval;
M = number of patients with data during the interval;
N = number of patients randomized and treated;
Wks = weeks.

Frequency of nausea and vomiting was higher in all three dulaglutide groups compared to placebo during all 3 time intervals. There was a dose-response in the frequency of nausea overall (Weeks 0-18) across the dulaglutide groups, with the greatest frequency in the dulaglutide 4.5 mg group (30.3%). In each dulaglutide treatment group, nausea was most frequent during the titration period (Week 0-6) and decreased from Weeks 6-10 and beyond. Prevalence of vomiting ranged from 6.6% to 8.9% across the dulaglutide groups during the titration period, and decreased during the Week 6-10 period. During all 3 time intervals, frequency of diarrhea was generally similar in the placebo and dulaglutide 1.5 mg groups and higher in the higher-dose groups. More frequent reporting of diarrhea in the dulaglutide 3.0 mg and 4.5 mg groups during the initial 6 weeks continued during the Week 6-10 period, and decreased thereafter. Incidence of diarrhea was greater in the higher-dose groups compared to the 1.5 mg group during the titration period before patients received the 3.0 mg or 4.5 mg doses; therefore, it appears that the differences were not entirely dose-related. In terms of incidence of severe nausea, diarrhea, and vomiting, few patients had any severe events, and incidence was generally similar in all four treatment groups.

Although the incidence of nausea, vomiting, and diarrhea was increased in patients treated with dulaglutide in a dose-dependent manner, and the proportion of patients discontinuing study treatment due to adverse events was higher in comparison to the dulaglutide 1.5 mg group, the difference in incidence between the high dose and 1.5 mg groups were modest, and the frequency of relevant GI events and treatment discontinuations was lower than those observed in completed dulaglutide trials of shorter duration that included patients who received nontitrated doses ≥3.0 mg, indicating the titration algorithms A1 and A2 had a beneficial effect.

The number of patients randomized by titration algorithm in the dulaglutide 3.0 mg and 4.5 mg groups are as follows: dulaglutide 3.0 mg A1, 41; dulaglutide 3.0 mg A2, 38; dulaglutide 4.5 mg A1, 39; dulaglutide 4.5 mg A2, 37. Table 3 summarizes frequency of nausea, vomiting, and diarrhea by dose and titration algorithm for the 2 higher dose groups, as measured by prevalence, incidence, and first onset of the events over 3 key time periods (Weeks 0-6 [titration period], Weeks 6-10, and Weeks 0-18 [treatment period]).

Summary of Prevalence, Incidence, and First Onset of Nausea, Vomiting, and Diarrhea by Dose and Titration Algorithm (Dulaglutide 3.0 mg and Dulaglutide 4.5 mg) and Time Period, Intent-to-Treat Population. Abbreviations: A1 = algorithm 1; A2 = algorithm 2; m = number of patients with event during the interval; M = number of patients with data during the interval; N = number of patients randomized and treated; Wks = weeks. Prevalence counts any patient who had a new or ongoing event during the interval. Incidence counts any patient who had an event begin during the interval. Onset counts any patient who had the first event of that type during the interval.

| Event/ Parameter/ Time Period | Treatment/Algorithm Groups | | | | Algorithm Groups | |
|---|---|---|---|---|---|---|
| | 3.0 A1 (N = 41) m/M (%) | 3.0 A2 (N = 38) m/M (%) | 4.5 A1 (N = 39) m/M (%) | 4.5 A2 (N = 37) m/M (%) | A1 (N = 80) m/M (%) | A2 (N = 75) m/M (%) |
| Nausea | | | | | | |
| Prevalence | | | | | | |
| Wks 0-6 | 11/41 (26.8) | 5/38 (13.2) | 7/39 (17.9) | 10/37 (27.0) | 18/80 (22.5) | 15/75 (20.0) |
| Wks 6-10 | 5/40 (12.5) | 3/38 (7.9) | 6/38 (15.8) | 8/37 (21.6) | 11/78 (14.1) | 11/75 (14.7) |
| Wks 0-18 | 12/41 (29.3) | 7/38 (18.4) | 11/39 (28.2) | 12/37 (32.4) | 23/80 (28.8) | 19/75 (25.3) |
| Incidence | | | | | | |
| Wks 0-6 | 11/41 (26.8) | 5/38 (13.2) | 7/39 (17.9) | 10/37 (27.0) | 18/80 (22.5) | 15/75 (20.0) |
| Wks 6-10 | 2/40 (5.0) | 3/38 (7.9) | 6/38 (15.8) | 4/37 (10.8) | 8/78 (10.3) | 7/75 (9.3) |
| Wks 0-18 | 12/41 (29.3) | 7/38 (18.4) | 11/39 (28.2) | 12/37 (32.4) | 23/80 (28.8) | 19/75 (25.3) |
| Onset | | | | | | |
| Wks 0-6 | 11/41 (26.8) | 5/38 (13.2) | 7/39 (17.9) | 10/37 (27.0) | 18/80 (22.5) | 15/75 (20.0) |
| Wks 6-10 | 1/40 (2.5) | 2/38 (5.3) | 3/38 (7.9) | 2/37 (5.4) | 4/78 (5.1) | 4/75 (5.3) |
| Wks 0-18 | 12/41 (29.3) | 7/38 (18.4) | 11/39 (28.2) | 12/37 (32.4) | 23/80 (28.8) | 19/75 (25.3) |
| Vomiting | | | | | | |
| Prevalence | | | | | | |
| Wks 0-6 | 6/41 (14.6) | 1/38 (2.6) | 3/39 (7.7) | 2/37 (5.4) | 9/80 (11.3) | 3/75 (4.0) |
| Wks 6-10 | 1/40 (2.5) | 1/38 (2.6) | 0/38 | 4/37 (10.8) | 1/78 (1.3) | 5/75 (6.7) |
| Wks 0-18 | 6/41 (14.6) | 2/38 (5.3) | 4/39 (10.3) | 6/37 (16.2) | 10/80 (12.5) | 8/75 (10.7) |
| Incidence | | | | | | |
| Wks 0-6 | 6/41 (14.6) | 1/38 (2.6) | 3/39 (7.7) | 2/37 (5.4) | 9/80 (11.3) | 3/75 (4.0) |
| Wks 6-10 | 1/40 (2.5) | 1/38 (2.6) | 0/38 | 3/37 (8.1) | 1/78 (1.3) | 4/75 (5.3) |
| Wks 0-18 | 6/41 (14.6) | 2/38 (5.3) | 4/39 (10.3) | 6/37 (16.2) | 10/80 (12.5) | 8/75 (10.7) |
| Onset | | | | | | |
| Wks 0-6 | 6/41 (14.6) | 1/38 (2.6) | 3/39 (7.7) | 2/37 (5.4) | 9/80 (11.3) | 3/75 (4.0) |
| Wks 6-10 | 0/40 | 1/38 (2.6) | 0/38 | 3/37 (8.1) | 0/78 | 4/75 (5.3) |
| Wks 0-18 | 6/41 (14.6) | 2/38 (5.3) | 4/39 (10.3) | 6/37 (16.2) | 10/80 (12.5) | 8/75 (10.7) |
| Diarrhea | | | | | | |
| Prevalence | | | | | | |
| Wks 0-6 | 7/41 (17.1) | 4/38 (10.5) | 6/39 (15.4) | 3/37 (8.1) | 13/80 (16.3) | 7/75 (9.3) |
| Wks 6-10 | 4/40 (10.0) | 6/38 (15.8) | 5/38 (13.2) | 4/37 (10.8) | 9/78 (11.5) | 10/75 (13.3) |
| Wks 0-18 | 8/41 (19.5) | 11/38 (28.9) | 9/39 (23.1) | 6/37 (16.2) | 17/80 (21.3) | 17/75 (22.7) |
| Incidence | | | | | | |
| Wks 0-6 | 7/41 (17.1) | 4/38 (10.5) | 6/39 (15.4) | 3/37 (8.1) | 13/80 (16.3) | 7/75 (9.3) |
| Wks 6-10 | 0/40 | 5/38 (13.2) | 5/38 (13.2) | 2/37 (5.4) | 5/78 (6.4) | 7/75 (9.3) |
| Wks 0-18 | 8/41 (19.5) | 11/38 (28.9) | 9/39 (23.1) | 6/37 (16.2) | 17/80 (21.3) | 17/75 (22.7) |
| Onset | | | | | | |
| Wks 0-6 | 7/41 (17.1) | 4/38 (10.5) | 6/39 (15.4) | 3/37 (8.1) | 13/80 (16.3) | 7/75 (9.3) |

The frequency of nausea is similar with A1 and A2 overall; there is a difference within the 3.0 mg group, with lower frequency within the A2 subgroup compared to the A1 subgroup, but this difference is considered unlikely to be related to the titration algorithms, as suggested by similar frequencies within the 4.5 mg group A1 and A2 subgroups. Most of the events of nausea occur during the titration period, with few new events reported upon uptitration to final doses (Weeks 6-10).

The frequency of vomiting is similar with A1 and A2 overall; more patients in the A1 subgroup than the A2 subgroup had events within the dulaglutide 3.0 mg group and more patients had events in the A2 subgroup than in the A1 subgroup within the dulaglutide 4.5 mg group, but, similar to nausea as described above, these differences are considered unrelated to the titration algorithms, since differences between the A1 and A2 subgroups in the 3.0 mg and 4.5 mg groups were in the opposite direction. Most of the events of vomiting with A1 occur during the titration period, with few new events reported upon uptitration to final doses (Weeks 6-10). With A2, the frequency of vomiting was lower during the titration period, remained at similar levels during the Week 6-10 period, and started decreasing after Week 10 and remained lower up to Week 18.

Prevalence and incidence of diarrhea during the titration period (Weeks 0-6) were higher in the dulaglutide 3.0 mg A1 and dulaglutide 4.5 mg A1 subgroups and lower in the dulaglutide 3.0 mg A2 and 4.5 mg A2 subgroups. During Weeks 6-10, prevalence and incidence were lower in the dulaglutide 3.0 mg A1 and dulaglutide 4.5 mg A2 subgroups and higher in the dulaglutide 3.0 mg A2 and dulaglutide 4.5 mg A1 subgroups.

The observed pattern of incidence of these events in A1 versus A2 suggest that starting with a lower dulaglutide dose (dulaglutide 0.75 mg [used in A2] vs. dulaglutide 1.5 mg [used in A1]) may reduce GI tolerability events during the titration period. Slower reduction in frequency of these events in the A2 group versus the A1 group during the final uptitration phase (Weeks 6-10) suggests a longer titration period may be needed to allow for development of tachyphylaxis to GI side effects of dulaglutide.

As noted above, earlier studies on doses of 3.0 mg and greater resulted in increases in pulse rate which contributed, in part, to discontinuation of the 3.0 mg arm in an earlier study. Thus, changes in pulse rate were also measured in the present study, and the data collected are provided in Table 4 below:

TABLE 4

Change from baseline in heart rate by treatment in ITT population.

| Time | LS mean change in PR (bpm) (95% CI) [n] | | | |
|---|---|---|---|---|
| (wks) | Placebo | Dula 1.5 | Dula 3.0 | Dula 4.5 |
| 2 | 0.22 (−1.50, 1.95) [80] | 1.77 (0.03, 3.50) [80] | 1.87 (0.12, 3.62) [79] | 1.91 (0.12, 3.70) [76] |
| 4 | −0.98 (−2.62, 0.66) [79] | 1.09 (−0.57, 2.75) [78] | 1.38 (−0.28, 3.05) [79] | 1.97 (0.25, 3.69) [74] |
| 6 | −1.97 (−3.71, −0.23) [76] | 0.52 (−1.22, 2.27) [77] | 1.72 (−0.04, 3.47) [77] | 2.07 (0.27, 3.87) [74] |
| 7 | −0.85 (−2.45, 0.75) [77] | 2.13 (0.50, 3.75) [76] | 2.37 (0.75, 4.00) [77] | 3.94 (2.27, 5.61) [74] |
| 8 | −0.06 (−1.90, 1.79) [76] | 1.83 (−0.03, 3.68) [76] | 1.86 (−0.00, 3.73) [76] | 4.70 (2.78, 6.62) [72] |
| 9 | 0.04 (−1.86, 1.77) [76] | 0.79 (−1.04, 2.62) [75] | 2.28 (0.44, 4.11) [76] | 3.85 (1.96, 5.75) [71] |
| 10 | −1.80 (−3.53, −0.08) [77] | 0.78 (−0.97, 2.52) [76] | 2.18 (0.43, 3.93) [77] | 2.65 (0.84, 4.46) [71] |
| 14 | 0.28 (−1.44, 2.00) [76] | −0.22 (−1.97, 1.53) [73] | 0.58 (−1.15, 2.31) [78] | 2.11 (0.29, 3.92) [69] |
| 18 | −1.40 (−3.20, 0.41) [75] | −0.71 (−2.55, 1.12) [72] | −0.04 (−1.86, 1.78) [75] | 0.70 (−1.18, 2.58) [70] |

Abbreviations: LS = least squares;
PR = pulse rate;
wks = weeks;
CI = confidence interval;
n = sample size.

As indicated in Table 4 above, mean changes in pulse rate across dulaglutide groups were similar during the entire treatment period and at the end of the study were similar.

In terms of determining the optimal dose titration strategy, patients who started treatment with dulaglutide 0.75 mg (for 2 weeks, A1) had fewer GI issues initially than patients who started on dulaglutide 1.5 mg (for 4 weeks, A2), but these differences were not maintained upon further uptitration to 1.5 mg with A1. Differences were also noted between A1 and A2 in the dulaglutide 4.5 mg group once the patients were uptitrated to their final doses (in the A1 arm from 3.0 mg to 4.5 mg; in the A2 arm from 1.5 mg to 4.5 mg), with tolerability modestly poorer in the patients in the A2 arm. These results suggest that further adjustments in the algorithms may be capable of optimizing dulaglutide titration with higher doses with respect to duration of titration and dose levels needed to further minimize the risk of tolerability issues.

Phase 3 Study.

A Phase 3, multicenter, randomized, double-blind, parallel-arm study is designed with 3 study periods (Lead-In, Treatment, and Safety Follow-up) in patients with T2D with inadequate glycemic control on metformin only; the study has a 52-week treatment duration, with primary endpoint at 36 weeks. The study is designed to assess the efficacy and safety of once weekly dulaglutide 3.0 mg and 4.5 mg in comparison to once weekly dulaglutide 1.5 mg.

A minimum sample size of approximately 1800 patients assuming 15% dropout rate are enrolled (randomized) in order to obtain approximately 510 completers per arm at 36 weeks. At Visit 3, patients are randomized in a 1:1:1 ratio to weekly injections of dulaglutide 4.5 mg, 3.0 mg, or 1.5 mg, in combination with stable doses of metformin. The investigational doses of 4.5 and 3.0 mg are administered following a titration algorithm designed based on PK/PD modeling of nausea and vomiting events from the Phase 2 study described above, with the goal of further alleviating gastrointestinal adverse events. PK/PD exposure-response modeling of the Phase 2 study data also predicts that the daily incidence of nausea and vomiting at higher dulaglutide doses would be lowest in algorithms starting at a 0.75 mg dose with a slower dose escalation over an 8-week period, allowing adequate time for tolerance to develop. Based on these findings, patients in the present study are titrated through sequential 4-week treatment segments beginning with 0.75 mg once weekly followed by 1.5 mg once weekly. At week 8, patients randomized to the dulaglutide 1.5 mg group continue on this dose for the remainder of the Treatment Period. Patients randomized to the dulaglutide 3.0 mg group are escalated to 3.0 mg once weekly at Week 8, and will continue on this dose for the remainder of the Treatment Period. Patients assigned to the dulaglutide 4.5 mg group are escalated to 3.0 mg once weekly at Week 8 for 4 weeks, followed by escalation to their final dose of 4.5 mg once weekly at Week 12. Study participants are treated for 52 weeks, with the primary objectives assessed at Week 36. This gradual, step-wise dose titration strategy is intended to further improve GI tolerability at the 3.0 mg and 4.5 mg doses relative to that observed in the Phase 2 study described above.

Formulation Stability Studies

A demonstration batch is prepared containing various concentrations of dulaglutide in the formulation used for the currently approved dulaglutide doses, and samples are filled into the commercial primary packaging for dulaglutide, as set forth in Table 5 below:

TABLE 5

Demonstration batch composition.

| | |
|---|---|
| Dulaglutide Concentration | 3.0, 6.0, 9.0, and 12.0 mg/mL |
| Sodium Citrate | 2.74 mg/mL |
| Citric Acid Anhydrous | 0.13 mg/mL |
| Mannitol | 46.4 mg/mL |
| Polsyorbate-80 | 0.02% |
| Primary Packaging | BD Gen 2 1 mL Long, West Uncoated Plunger |

Samples are placed on stability for up to 24 months. After 3 months, however, the study was discontinued due to observed decreases in the level of PS80. The data obtained on PS80 concentrations are analyzed in JMP 12.1.0 software for predicting PS80 content in 24-month long-term storage condition. Activation energy ($E_a$) of PS80 degradation is calculated and used for predicting PS80 content over long-term storage. Based on a second-degree polynomial model, the point estimate for activation energy, $E_a$, is 15.24 kcal/mol and the lower 95% confidence limit was 12.85 kcal/mol. Based on this analysis, with starting PS80 level at 0.02% (w/v), the 24-month prediction of PS80 for the 12 mg/mL dulaglutide formulation is predicted to be below the specification limit for current commercial dulaglutide. The 24-month prediction of PS80 for the 9 mg/mL dulaglutide formulation would also be close to the specification limit.

In order to evaluate the risk of PS80 content out-of-specification (OOS) during 24 months of long-term storage, a Monte Carlo simulation is performed in R 3.4.0 software, leveraging historical dulaglutide data. The OOS risks associated with each high concentration level are summarized in Table 6 below:

TABLE 6

Monte Carlo Simulation Results for 24-month PS80 OOS Risk.

| Dulaglutide Concentration | Probability of PS80% (w/v) OOS after 24 months 2-8° C. Storage | |
|---|---|---|
| | $E_a = 15.24$ | $E_a = 12.85$ |
| 6 mg/mL | $5 \times 10^{-5}$ | 0.06692 |
| 9 mg/mL | 0.10279 | 0.96191 |
| 12 mg/mL | 0.89239 | 1 |

The results from the Monte Carlo simulation showed excessive degradation using the asymptotic lower confidence limit of the activation energy and thus high-risk levels for shelf-life OOS. PS80 is present in the dulaglutide formulation to provide protection against physical stress, and the PS80 lower specification limit was set to ensure sufficient PS80 is present throughout maximum possible shelf-life and in-use periods to provide that physical protection.

In view of the preliminary data analysis from the development stability study indicating that polysorbate-80 hydrolysis was increased in the higher strength dulaglutide formulations, it was determined to explore modifications to the formulation. Increasing the level of polysorbate-80 in the formulation may result in adequate intact polysorbate-80 at end-of-shelf life, but the hydrolysis of higher amounts of polysorbate-80 may result in appearance of visible particles. Thus, a surfactant range study was initiated in order to assess the impact of varying levels of surfactant on stability.

Samples were prepared containing dulaglutide concentrations of 3, 6, 9 and 12 mg/mL, 10 mM citrate buffer, 46.4 mg/mL mannitol and PS80 concentrations ranging from 0.002% to 0.05%, filled into vials, and placed on stability at 30° C. Samples are pulled at 0, 12, 25, 35, 46 and 74 days and tested for free oleic acid (FOA)—a hydrolysis product of PS80—and particulate matter. Data show an increase in FOA with increasing rates for higher dulaglutide strength formulations. At the same concentration of dulaglutide, the increased rates of FOA are the same for formulations having 0.02% and 0.05% starting level of polysorbate-80. Particulate matter, as measured by micro-flow imaging (MFI) is equivalent for all formulations, regardless of dulaglutide or polysorbate-80 level. The results support the ability to increase starting levels of polysorbate-80—as much as 0.05% without compromising dulaglutide stability.

Based on results of the development stability study and the surfactant study, a detailed statistical analysis is conducted of all available data. The analysis concludes that the level of starting polysorbate-80 in the formulation, for the 6.0 and 9.0 mg/mL strengths, should be increased from 0.02% to 0.025% (w/v). This increased level is selected to provide high probability that even at end-of-shelf life, there will be sufficient polysorbate-80—meet the current approved specifications for commercial product.

A second demonstration batch is prepared containing the same concentrations as used in the first demonstration batch described above, with the exception of an increase in PS80 concentration, as set forth in Table 7 below:

TABLE 7

Second demonstration batch parameters.

| | |
|---|---|
| Dulaglutide Concentration | 3.0, 6.0, 9.0, and 12.0 mg/mL |
| Sodium Citrate | 2.74 mg/mL |
| Citric Acid Anhydrous | 0.13 mg/mL |
| Mannitol | 46.4 mg/mL |
| Polsyorbate-80 | 0.025% |
| Primary Packaging | BD Gen 2 1 mL Long Syringe, West Uncoated Plunger |

Samples are placed on stability at 5° C., 25° C. and 30° C. Results from samples held up to six months at 5° C. and 25° C. and one month at 30° C. indicate that the concentrated formulations are chemically and physically stable, and that the PS80 concentration will remain above the lower specification limit throughout shelf-life.

We claim:

1. A method of improving glycemic control in a subject in need thereof with type 2 diabetes comprising:
   a) administering to said subject an initial dose of 0.75 mg of dulaglutide once weekly;
   b) increasing the dose to 1.5 mg of dulaglutide once weekly;
   c) increasing the dose to 3.0 mg of dulaglutide once weekly after at least 4 weeks on the 1.5 mg dose; and
   d) increasing the dose to 4.5 mg of dulaglutide once weekly after at least 4 weeks on the 3.0 mg dose.

2. The method of claim 1, wherein the dose increases of each of steps b) through d) are performed when there is a need to reduce the subject's HbA1c level.

3. The method of claim 2, wherein administration of 4.5 mg of dulaglutide once weekly results in a greater body weight reduction than administration of 1.5 mg of dulaglutide once weekly.

* * * * *

SEQUENCE LISTING

<160> NUMBER OF SEQ ID NOS: 1

<210> SEQ ID NO 1
<211> LENGTH: 275
<212> TYPE: PRT
<213> ORGANISM: Artificial Sequence
<220> FEATURE:
<223> OTHER INFORMATION: Synthetic Construct

```
<400> SEQUENCE: 1

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
                20                  25                  30

Gly Gly Gly Ser Gly Gly Gly Gly Ser Gly Gly Gly Gly Ser Ala Glu
            35                  40                  45

Ser Lys Tyr Gly Pro Pro Cys Pro Pro Cys Pro Ala Pro Glu Ala Ala
    50                  55                  60

Gly Gly Pro Ser Val Phe Leu Phe Pro Pro Lys Pro Lys Asp Thr Leu
65                  70                  75                  80

Met Ile Ser Arg Thr Pro Glu Val Thr Cys Val Val Val Asp Val Ser
                85                  90                  95

Gln Glu Asp Pro Glu Val Gln Phe Asn Trp Tyr Val Asp Gly Val Glu
            100                 105                 110

Val His Asn Ala Lys Thr Lys Pro Arg Glu Glu Gln Phe Asn Ser Thr
        115                 120                 125

Tyr Arg Val Val Ser Val Leu Thr Val Leu His Gln Asp Trp Leu Asn
    130                 135                 140

Gly Lys Glu Tyr Lys Cys Lys Val Ser Asn Lys Gly Leu Pro Ser Ser
145                 150                 155                 160

Ile Glu Lys Thr Ile Ser Lys Ala Lys Gly Gln Pro Arg Glu Pro Gln
                165                 170                 175

Val Tyr Thr Leu Pro Pro Ser Gln Glu Glu Met Thr Lys Asn Gln Val
            180                 185                 190

Ser Leu Thr Cys Leu Val Lys Gly Phe Tyr Pro Ser Asp Ile Ala Val
        195                 200                 205

Glu Trp Glu Ser Asn Gly Gln Pro Glu Asn Asn Tyr Lys Thr Thr Pro
    210                 215                 220

Pro Val Leu Asp Ser Asp Gly Ser Phe Phe Leu Tyr Ser Arg Leu Thr
225                 230                 235                 240

Val Asp Lys Ser Arg Trp Gln Glu Gly Asn Val Phe Ser Cys Ser Val
                245                 250                 255

Met His Glu Ala Leu His Asn His Tyr Thr Gln Lys Ser Leu Ser Leu
            260                 265                 270

Ser Leu Gly
        275
```